United States Patent
Seltzer et al.

(10) Patent No.: US 10,228,336 B2
(45) Date of Patent: Mar. 12, 2019

(54) MOBILE NMR SENSOR FOR ANALYZING SUBSURFACE SAMPLES

(71) Applicant: Chevron U.S.A. Inc., San Ramon, CA (US)

(72) Inventors: Scott J. Seltzer, Houston, TX (US); Boqin Sun, Houston, TX (US); Haijing Wang, Sugar Land, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 596 days.

(21) Appl. No.: 14/841,851

(22) Filed: Sep. 1, 2015

(65) Prior Publication Data

US 2017/0059497 A1    Mar. 2, 2017

(51) Int. Cl.
| | |
|---|---|
| *G01N 24/08* | (2006.01) |
| *G01R 33/44* | (2006.01) |
| *G01V 3/32* | (2006.01) |
| *G01R 33/38* | (2006.01) |
| *G01R 33/341* | (2006.01) |
| *G01R 33/383* | (2006.01) |

(52) U.S. Cl.
CPC ....... *G01N 24/081* (2013.01); *G01R 33/3808* (2013.01); *G01R 33/341* (2013.01); *G01R 33/383* (2013.01); *G01R 33/448* (2013.01)

(58) Field of Classification Search
CPC .............. G01N 24/081; G01R 33/3808; G01R 33/448; G01R 33/383; G01R 33/341
See application file for complete search history.

(56) References Cited

U.S. PATENT DOCUMENTS

| | | | | |
|---|---|---|---|---|
| 4,933,638 A | * | 6/1990 | Kleinberg | G01N 24/081 324/303 |
| 5,930,606 A | * | 7/1999 | McCulloch | B23K 26/032 438/157 |
| 5,952,830 A | * | 9/1999 | Petropoulos | G01R 33/385 324/318 |
| 6,489,767 B1 | | 12/2002 | Prado et al. | |
| 7,095,230 B2 | | 8/2006 | Blümich et al. | |
| 7,358,734 B2 | | 4/2008 | Blümich et al. | |
| 8,009,001 B1 | * | 8/2011 | Cleveland | H02P 6/14 310/156.31 |
| 8,461,836 B2 | | 6/2013 | Blank et al. | |
| 8,519,708 B2 | * | 8/2013 | Prado | G01N 24/08 324/309 |

(Continued)

OTHER PUBLICATIONS

Blümich, B., et al.; "Degradation of Historical Paper: Nondestructive Analysis by the NMR-MOUSE"; 2003, Journal of Magnetic Resonance, vol. 161, pp. 204-209.

(Continued)

*Primary Examiner* — Huy Q Phan
*Assistant Examiner* — Zannatul Ferdous

(57) ABSTRACT

An NMR sensor and method is disclosed for analyzing a core sample from a subsurface formation. Embodiments of the method utilize two or more magnets disposed proximate to each other. The configuration of the magnets allows for increased detection frequency, and creates a strong field with much finer resolution than existing designs. In addition, embodiments of the sensor may be used at the well site due to its small size and simple hardware. Further details and advantages of various embodiments of the method are described in more detail herein.

45 Claims, 16 Drawing Sheets

(56) References Cited

U.S. PATENT DOCUMENTS

| | | | | |
|---|---|---|---|---|
| 9,098,889 B2* | 8/2015 | Zhao | ............... | G06T 7/0004 |
| 2005/0030021 A1* | 2/2005 | Prammer | ............ | G01N 24/081 |
| | | | | 324/303 |
| 2011/0184711 A1* | 7/2011 | Altman | ............... | E21B 49/005 |
| | | | | 703/10 |
| 2014/0084927 A1* | 3/2014 | Walsh | ............... | G01N 24/081 |
| | | | | 324/319 |
| 2014/0225607 A1* | 8/2014 | Edwards | ............ | G01N 24/081 |
| | | | | 324/303 |
| 2014/0346886 A1* | 11/2014 | Yang | ............... | G06K 19/07779 |
| | | | | 307/104 |

OTHER PUBLICATIONS

Casanova, Federico, et al; "Single-Sided NMR"; Springer Science+Business Media; *Entire Book*, attached hereto for reference are pp. Cover Page, Introduction pages, Preface (pp. v-vii), Table of Contents (pp. ix-xii), Contributors (pp. xiii), and Chapter 1 (pp. 1-10).

Eidmann, G., et al.; "The NMR MOUSE, a Mobile Universal Surface Explorer"; 1996, Journal of Magnetic Resonance, Series A, vol. 122, pp. 104-109.

Manz, B., et al.; "A Mobile One-Sided NMR Sensor With a Homogeneous Magnetic Field: The NMR-MOLE"; 2006, Journal of Magnetic Resonance, vol. 183, pp. 25-31.

Van Landeghem, Maxime, et al.; "Low-Gradient Single-Sided NMR Sensor for One-Shot Profiling of Human Skin"; 2012, Journal of Magnetic Resonance, vol. 215, pp. 74-84.

* cited by examiner

MOBILE NMR SENSOR FOR ANALYZING SUBSURFACE SAMPLES

CROSS-REFERENCE TO RELATED APPLICATIONS

Not applicable.

STATEMENT REGARDING FEDERALLY SPONSORED RESEARCH OR DEVELOPMENT

Not applicable

BACKGROUND

Field of the Invention

This invention relates generally to the field of geological exploration for hydrocarbons. More specifically, the invention relates to a method of determining petrophysical properties of rock samples.

Background of the Invention

Traditionally, nuclear magnetic resonance (NMR) devices are designed to enclose a sample, producing a strong, homogeneous magnetic field that is used to analyze that sample for purposes including chemical analysis and anatomical imaging. The reverse ("inside-out" or "single-sided") geometry, where the sample is located outside the NMR device, is technologically more challenging because of the difficulty in generating a homogeneous field over a large spatial region outside the magnet; as a result, NMR spectral linewidths tend to be too broad for chemical analysis, and images tend to be very blurry and have distortions. One area in which single-sided NMR has found application is oilfield borehole logging, where fluid typing is conducted within a small, shallow region in an underground rock formation in order to locate and characterize deposits of extractable hydrocarbon materials. Rather than the high magnetic fields (1 Tesla (T) or higher) used by most chemical and medical devices, logging tools employ "low-field" detection (generally below 1 T), with a field generated by one or more permanent magnets and detection occurring over a range of several inches into the formation wall. Fluids are characterized based on their diffusion and spin relaxation properties, a modality that is compatible with the field inhomogeneity endemic to the tool configuration. Recently, there has been increasing development on single-sided NMR devices for portable applications such as materials analysis. These tend to be designed for more general applicability than the specialized logging tools, although they operate on the same basic principles. Currently, there is no sensor available that provides a high-resolution porosity map of a subsurface rock sample, which will be critical for integrating the measured petrophysical properties and performing multi-scale analysis on the range of micro to field scale. A single-sided NMR sensor is the only solution for efficiently measuring a porosity map on the millimeter-to-centimeter scale.

Consequently, there is a need for improved sensors and methods to analyze rock and/or core samples from subsurface formations.

BRIEF SUMMARY

An NMR sensor and method is disclosed for analyzing a core sample from a subsurface formation. Embodiments of the method can utilize two or more magnets disposed adjacent to each other. The configuration of the magnets allows for increased detection frequency, and creates a strong field with much finer resolution than existing designs. In addition, embodiments of the sensor may be used at the well site due to its small size and simple hardware. Further details and advantages of various embodiments of the method are described in more detail herein.

In an embodiment, a nuclear magnetic resonance (NMR) sensor comprises two or more permanent magnets disposed proximate to each other. The magnets are configured to create a magnetic field. The sensor further comprises a sample holding member coupled to the magnets for holding a core sample. The magnetic field is located in a position between the magnets and proximate the surface of the sample holding member. The sensor also comprises an antenna disposed in between the magnets.

In another embodiment, a system for analyzing a sample from a subsurface formation comprises an NMR sensor comprising two or more permanent magnets disposed proximate to each other. The magnets are configured to create a magnetic field. The sensor further comprises a sample holding member coupled to the magnets for holding a core sample. The magnetic field is located in a position between the magnets and proximate the surface of the sample holding member. The sensor also comprises an antenna disposed in between the magnets. The system additionally comprises an interface for receiving one or more user inputs. The system also comprises a memory resource. The system further comprises input and output functions for presenting and receiving communication signals to and from a human user. In addition, the system comprises one or more central processing units for executing program instructions and program memory, coupled to the central processing unit, for storing a computer program including program instructions that, when executed by the one or more central processing units, cause the computer system to perform a plurality of operations for analyzing a fluid or core sample from a subsurface formation.

In another embodiment, a method of analyzing a sample from a subsurface formation, the method comprises a) extracting a sample from a subsurface formation. The method also comprises b) using a NMR sensor to scan the sample to determine one or more properties of the sample. The NMR sensor comprises two or more permanent magnets disposed proximate to each other. The magnets are configured to create a magnetic field. The sensor further comprises a sample holding member coupled to the magnets for holding a core sample. The magnetic field is located in a position between the magnets and proximate the surface of the sample holding member. The sensor also comprises an antenna disposed in between the magnets.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Figure 1A:
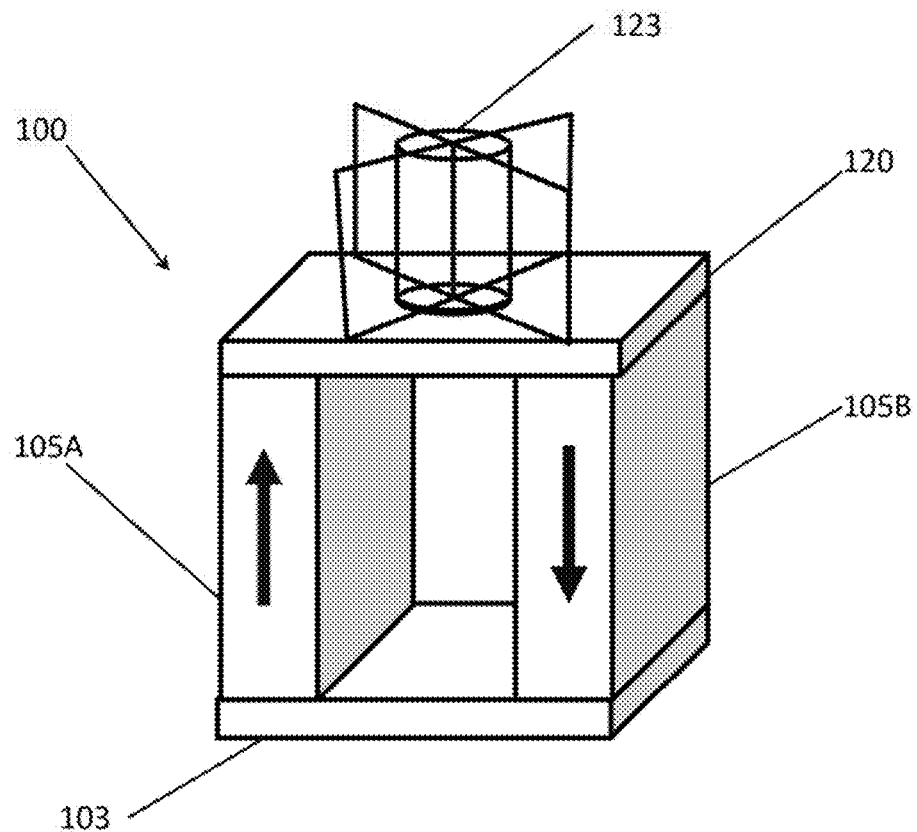
FIG. 1A illustrates an embodiment of an NMR sensor.

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections.

DETAILED DESCRIPTION OF THE PREFERRED EMBODIMENTS

Referring now to the Figures, embodiments of the disclosed methods will be described. As a threshold matter, embodiments of the methods may be implemented in numerous ways, as will be described in more detail below, including for example as a system (including a computer processing system), a method (including a computer implemented method), an apparatus, a computer readable medium, a computer program product, a graphical user interface, a web portal, or a data structure tangibly fixed in a computer readable memory. Several embodiments of the disclosed methods are discussed below. The appended drawings illustrate only typical embodiments of the disclosed methods and therefore are not to be considered limiting of its scope and breadth.

In an embodiment, referring to FIGS. 1A-1F, sensor 100 generally includes permanent magnets 105A-105B, a sample holding member 120, antenna 125, wall members 115, 117, and base 103. In this embodiment or arrangement, as better shown in FIG. 1C, which depicts an exploded view of an embodiment of sensor 100, wall members 113, 114, 115, 117 enclose two or more magnets 105A-105B. Base 103 supports magnets 105A-105B and may be coupled to magnets 105A-105B. Sample holding member 120 is disposed on magnets 105A-105B and the geological samples may be placed on sample holding member 120 so as to coincide with the "sweet spot" 123, shown in FIG. 1A. Antenna 125 may be coupled to sample holding member 120. In an embodiment, antenna 125 is coupled beneath member 120 and may be disposed or positioned in between magnets 105A-105B.

Figure 1B:
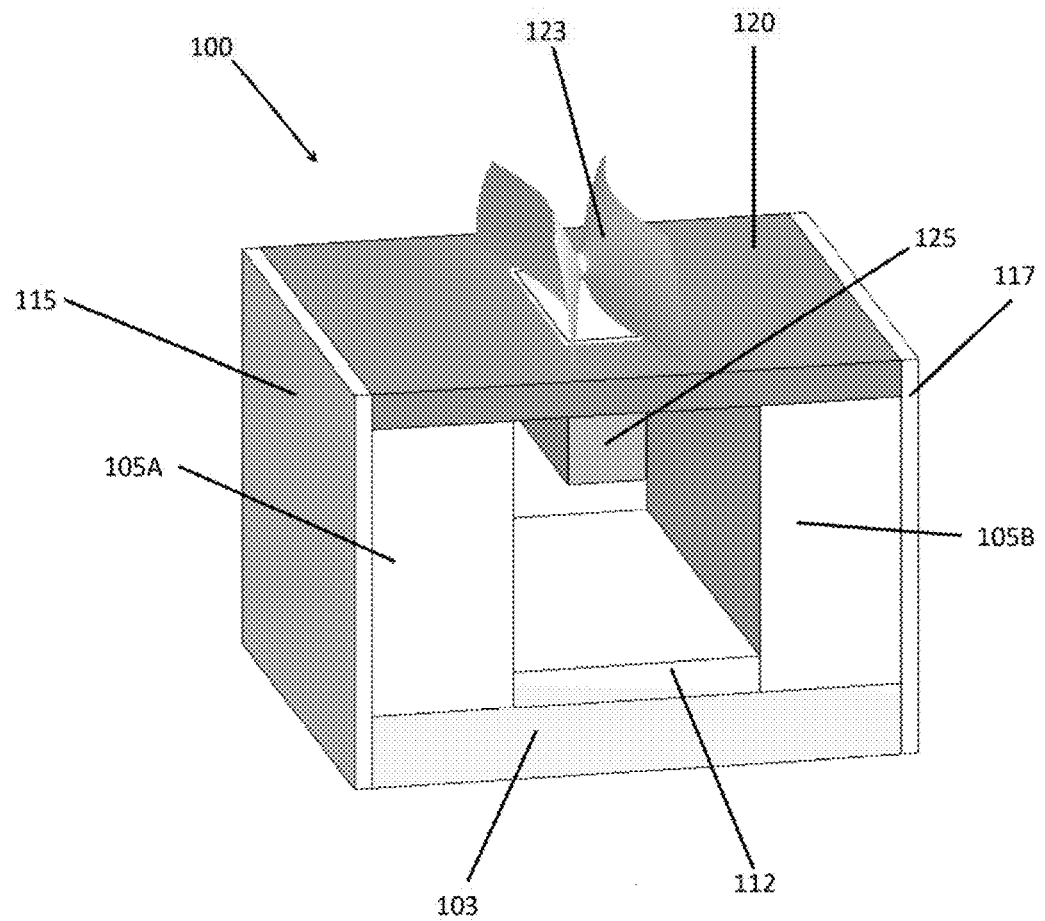
FIG. 1B illustrates another view of an embodiment of an NMR sensor.

As shown in FIGS. 1A-F, embodiments of the apparatus 100 may contain two or more permanent magnets 105A-105B. In an embodiment, the magnets may be neodymium magnets. Neodymium magnets may be used because of their very large remnant magnetization to produce a strong field and thus large NMR signal. However, any magnets known to those of skill in the art may be used. In an embodiment, the magnets can be permanent magnets. More specifically, examples of permanent magnets include without limitation, neodymium magnets, rare earth magnets, ceramic magnets, iron alloy magnets, or combinations thereof. In an embodiment, magnets 105A-105B may be cuboidal in geometry (i.e. have a rectangular cross-section). However, other suitable geometries known to those of skill in the art may be used. In one embodiment, the magnets 105A-105B may have dimensions of 1"×1"×2" (with magnetization along one of the short axes). However, magnets 105A-105B may be constructed or configured with any suitable dimensions. The remnant magnetization or magnetic strength of the magnets, the physical size, and spacing of the magnets help determine the magnetic field profile, and thus the sweet spot size, shape, and field strength. Accordingly, these parameters may all be configured in order to achieve the desired sweet spot size, shape, and field strength for the sensor 100. As used herein, the "sweet spot" 123, as shown in FIG. 1B, refers to the region of the sensor 100, distributed around the local extremum in the magnetic field strength, where the magnetic field is most uniform and so the largest volume of spins can be excited and detected simultaneously. Although shown in the center of the sensor 100 in the Figures, the sweet spot 123 may be located in any position of the sensor 100 according to the configuration of magnets 105A-105B. The core or fluid samples to be analyzed are generally disposed or placed in the sweet spots 123 for analysis. In an embodiment, sweet spot 123 may be disposed proximate to the member 120 so that the sweet spot 123 coincides with location of member 120. In this way, a sample may be placed on the member 120 for analysis.

Generally, the magnets are disposed proximate to each other so as to create a sweet spot. In other words, "proximate" in this context means the magnets 105A-105B are within sufficiently close vicinity to each other to create a magnetic field and a sweet spot. In an embodiment, the magnets 105A-105B may be arranged in parallel as shown in FIG. 1A, with magnetic fields aligned vertically but with opposite polarity or in the opposite direction as indicated by the arrows. This alignment generates a strong field above the device, pointing parallel to the direction between the magnets. The field in such an embodiment has maximum homogeneity at a saddle point 123, depicted by the curved surfaces in this region, creating a sweet spot that serves as the detection volume for the NMR measurement.

Magnets 105A, 105B may have any suitable magnetic strength. In some embodiments, the magnets may have a magnetic strength ranging from about 0.1 Tesla (T) to about 2.0 T, alternatively, from about 0.2 T to about 1.7 T, alternatively from about 0.5 T to about 1.5 T.

In an embodiment, a magnetic metallic base member 103 may act as the base of the sensor 100, returning the magnetic flux lines between the magnets 105A-105B to enhance the strength of the field at the sweet spot 123. Base member 103 may be made of any metallic magnetic material known to those of skill in the art. Examples may include without limitation, iron, steel, nickel, cobalt, gadolinium, any ferromagnetic metal alloys, or combinations thereof. The detection region profile is well-suited for both wellsite (onsite) and laboratory measurements, combining both a large detection volume for high signal-to-noise with high spatial resolution. In contrast, many existing devices exhibit a broad, flat measurement profile which may be ideal for high vertical resolution, but provide poor lateral resolution.

A spacer 112 may be disposed between magnets 105A-105B. Spacer 112 may serve to provide physical support between magnets 105A-105B to prevent magnets 105A-105B from attaching to each other. In embodiments, spacer 112 may be made of a non-magnetic material. Examples may include without limitation, nylon, polytetrafluoroethylene (PTFE), polyaryletherketone (PAEK), and/or other polymers. Spacer 112 may be configured with any shape suitable to fit in between magnets 105A-105B.

Figure 1C:
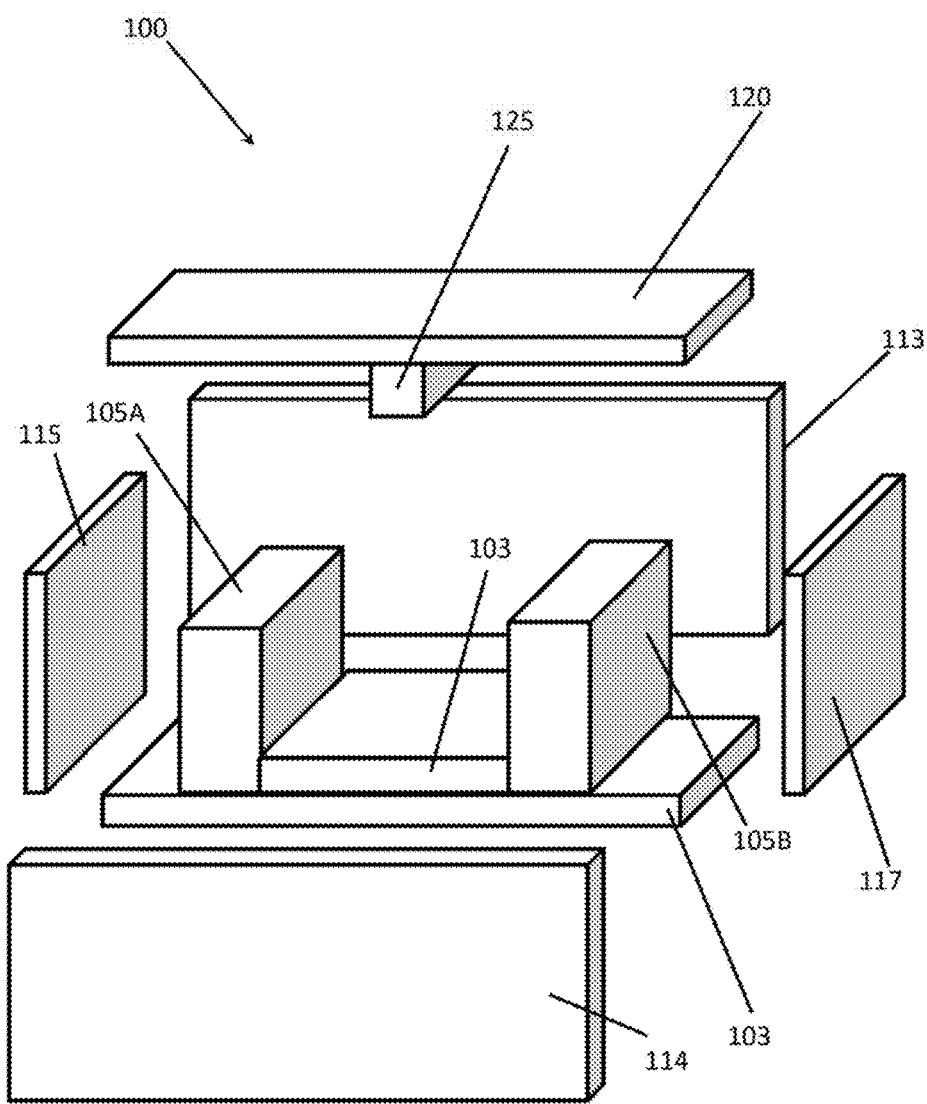
FIG. 1C illustrates an exploded perspective view of an embodiment of an NMR sensor.
Figure 1D:
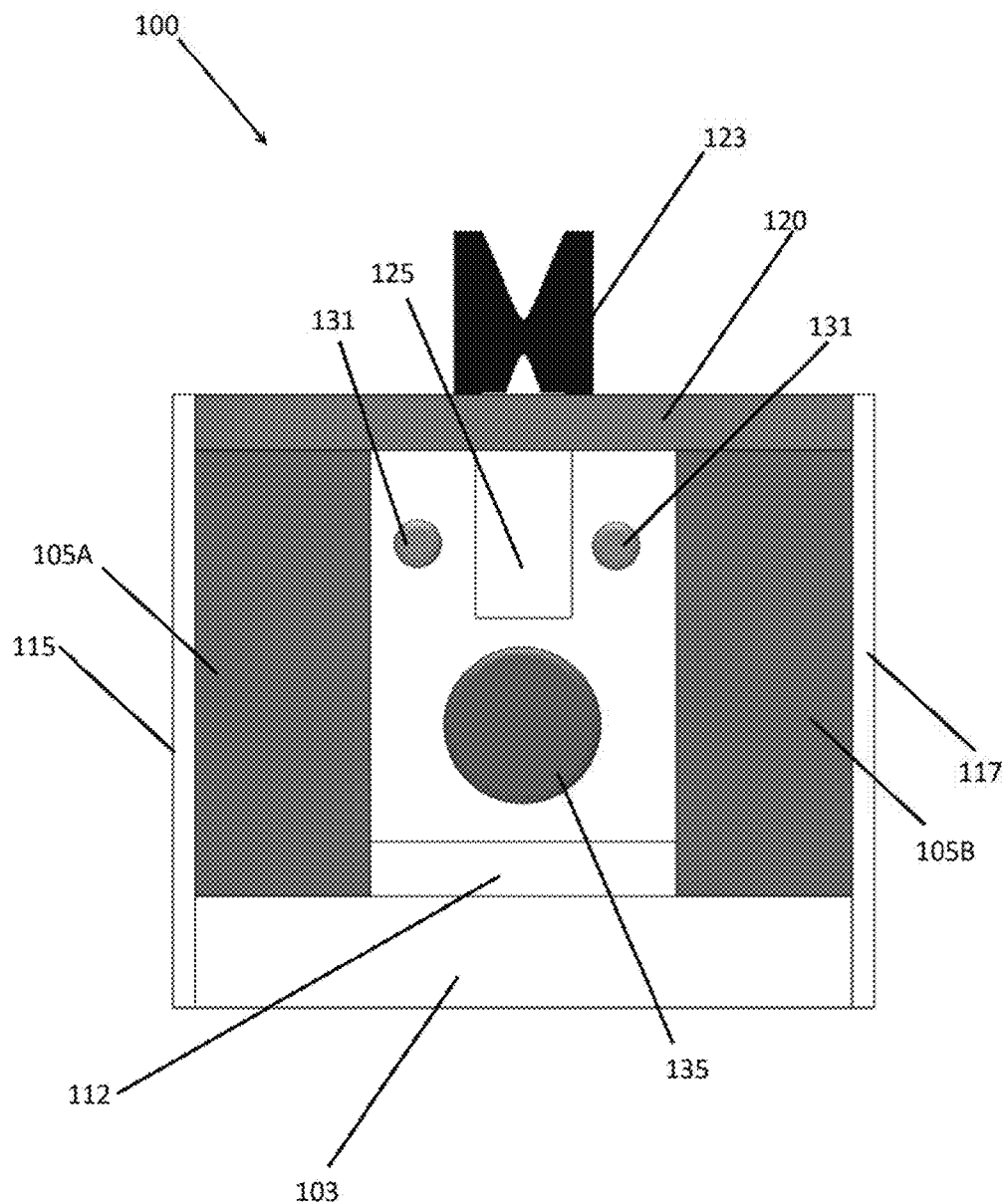
FIG. 1D illustrates a cross-sectional view of another embodiment of an NMR sensor.
Figure 1E:
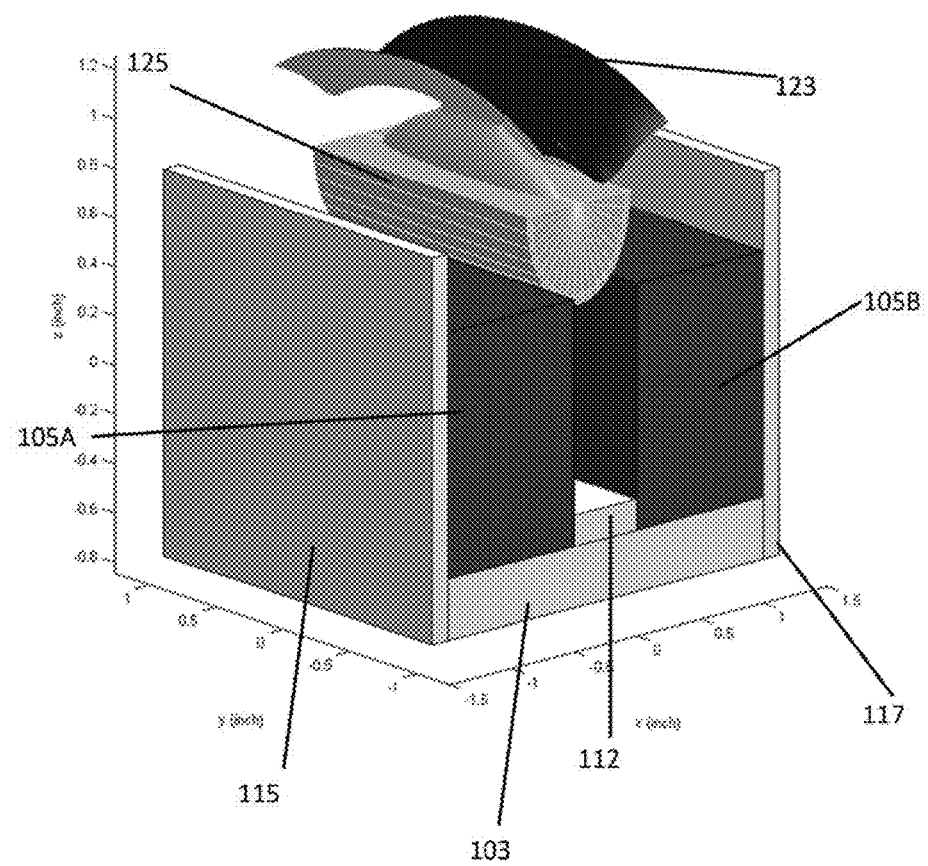
FIG. 1E illustrates an embodiment of the NMR sensor with a cylindrical antenna.
Figure 1F:
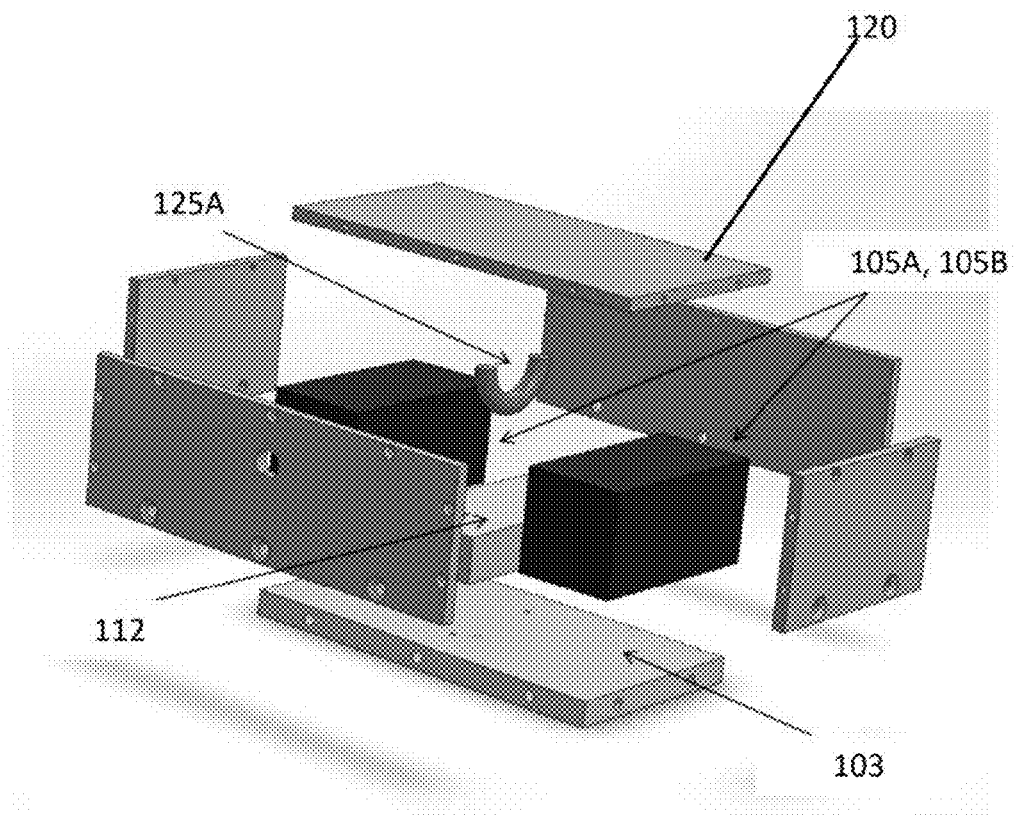
FIG. 1F illustrates an embodiment of the NMR sensor with a semi-toroidal antenna

In an embodiment, antenna 125 may be coupled to sample holding member 120. As shown in FIGS. 1B-D, antenna 125 is depicted as having a cuboidal geometry. However, it is contemplated antenna 125 may be any suitable geometry such as without limitation, rectangular, toroidal, circular, semi-circular, hemispherical, etc. In an embodiment, antenna 125 is a radiofrequency (RF) antenna. Generally, antenna 125 may be positioned in between magnets 105A-105B and beneath member 120. However, it is contemplated that antenna 125 may be disposed in any position on the member 120. In embodiments, antenna 125 can be a coil or wire that is wound around a holder, which may be fabricated from ferrite or any other suitable material. In other embodiments, antenna 125 may be fabricated using printed circuit boards (PCBs) mounted on the top of the device. In some embodiments, the sensitive region of the coil may not overlap with the sweet spot of the magnet. In other embodiments, the sensitive region of the coil may overlap with the sweet spot of the magnet. In another embodiment, antenna 125 may have a semi-cylindrical geometry such as shown in FIG. 1E. In an embodiment, sensor 100 may include an internal antenna, to prevent the exposure of the antenna to fluids during measurement. In one embodiment, antenna 125 may have a semi-toroidal geometry as shown in FIG. 1F. The semi-toroid antenna 125A may be made of a high-permeability material, such as ferrite or iron powder, shaped to capture magnetic flux from a particular sensing zone that coincides with the sweet spot of the magnets. As used herein, high-permeability refers to a material with a relative magnetic permeability of at least 10. This may serve to guide the magnetic flux from the sweet spot to the inside of the device, concentrating the NMR signal so that it can be detected by a coil wrapped around the torus; similarly, it will guide fields produced by the antenna to the sweet spot for optimal spin excitation.

Figure 1G:
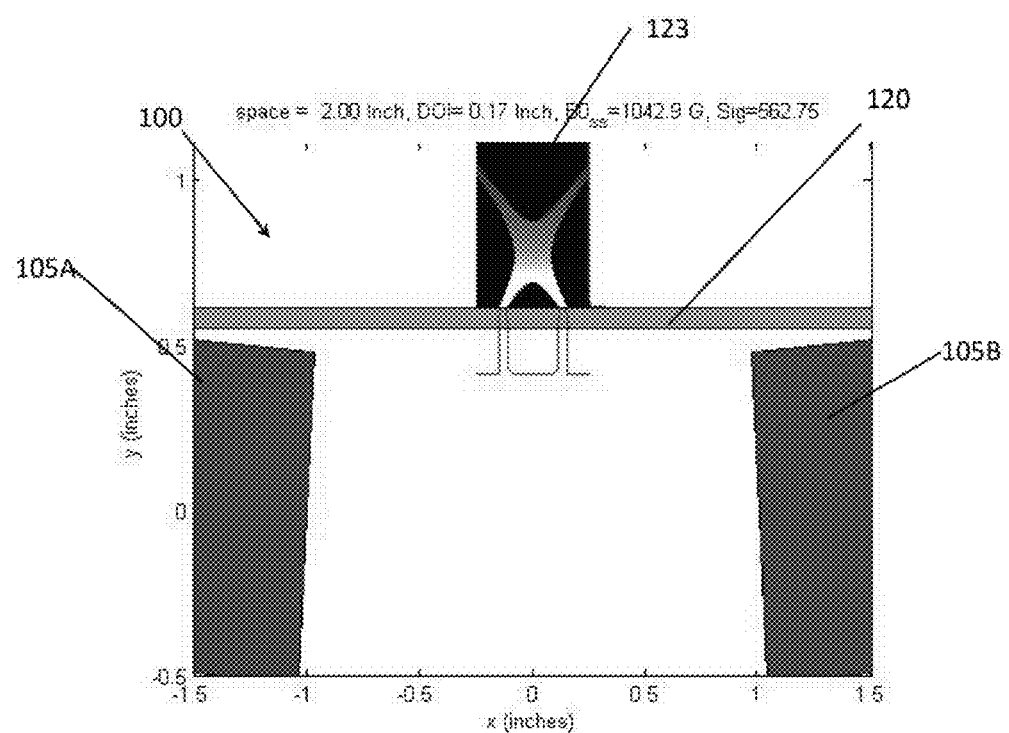
FIG. 1G illustrates an embodiment of the NMR sensor with tilted or angled magnets, including a computer simulation of the sweet spot of the sensor.

FIG. 1G illustrates another embodiment of sensor 100 in which magnets 105A-105B are angled or tilted. In this embodiment, magnets 105A-105B may be angled at any suitable angle. The magnets may be angled toward one another or away from one another. By considering the field strength, spot size, and relative NMR signal intensity, this embodiment shows that the sensor can be tailored for the design for a particular application. For example, a larger sweet spot size may correlate with the spot being further away from the magnets. By tilting the magnets inward, as in FIG. 1G, the sweet spot can be brought closer to the device without significant loss in size; compare with the sweet spot shown in FIG. 1H, which presents the case with the same conditions as FIG. 1G except the magnets are not tilted.

Figure 2:
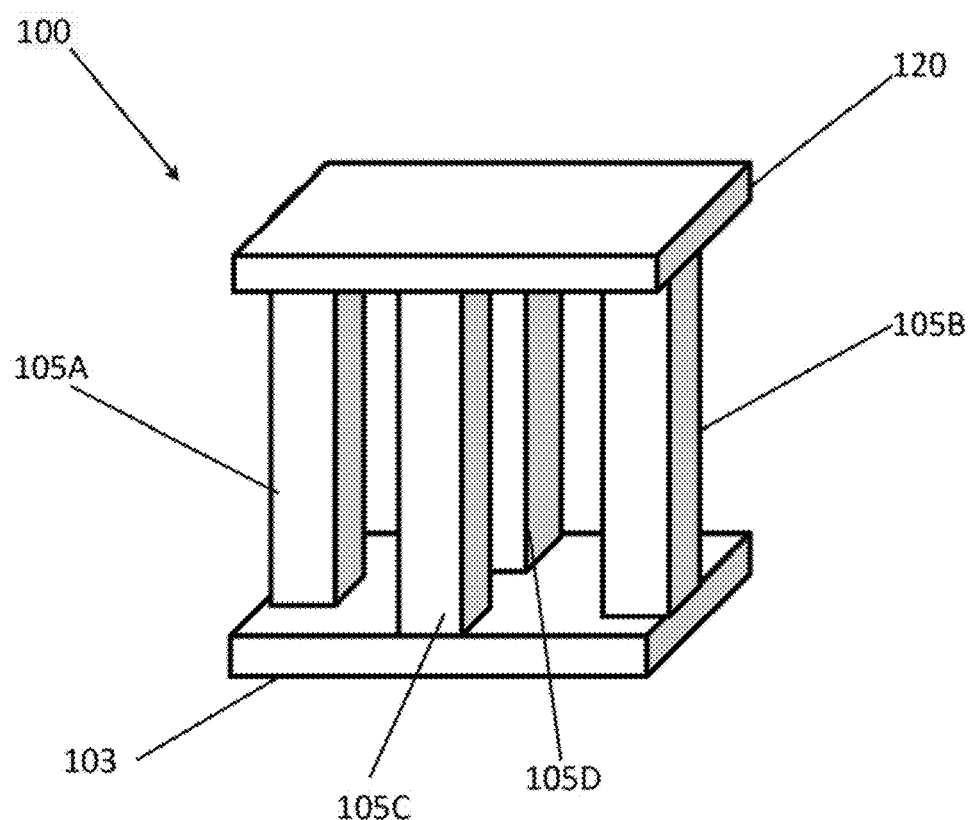
FIG. 2 illustrates another embodiment of the NMR sensor.

FIG. 2 illustrates another schematic of an embodiment of sensor 100 with additional magnets 105A-105D. In this embodiment, sensor 100 includes four magnets 105-15D arranged in a rectangular array. However, any number of additional magnets may be used and/or configured as desired.

Figure 8:
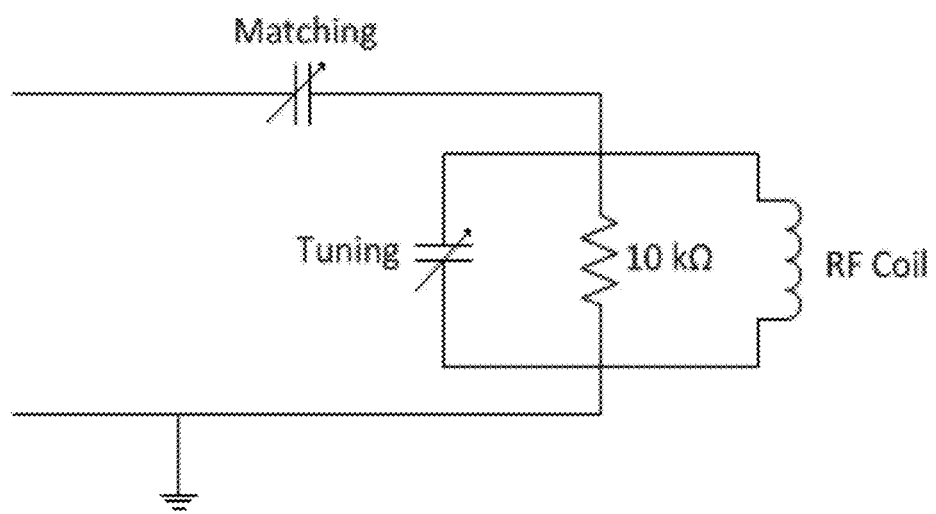
FIG. 8 illustrates a schematic of a tuning circuit that may be used with embodiments of the NMR sensor.

Referring now to FIGS. 1D and 8, a tuning circuit may be used with embodiments of the NMR sensor to achieve the radiofrequency (RF) amplitudes and pulses. Specifically, sensor 100 may include a tuning capacitor 135 disposed within sensor 100. Alternatively, the tuning circuit can be disposed external to sensor 100. In addition, wires 131 may be disposed within sensor 100. In an embodiment, wires 131 may serve as an antenna. In an embodiment, as shown in FIG. 1D, capacitor 100 and wires 131 may be located in between magnets 105A-105B. In an embodiment, the capacitances can be set by variable capacitors in parallel with fixed capacitors, to give adjustability around a central value. The values for the tuning and matching capacitances can be determined empirically, as they are determined by a combination of factors including the properties of the RF coil, the sample, and any cables used.

In an embodiment of a method of using sensor, the sensor 100 can be scanned either manually or automatically over the surface of a rock sample to create a high-resolution map of porosity, with voxel size determined by the spatial resolution of the sensor and the spacing of the measurements. These porosity values can be combined with other petrophysical measurements, such as resistivity, permeability, and hardness, taken at the same locations to create an overall petrophysical model of the sample. For example, as a compliment to the current, time-consuming practice of shipping core samples from the wellsite to the laboratory for high-quality NMR testing, a mobile NMR device incorporating sensor 100 can be quickly scanned (manually or automatically) over the entire length of core extracted from a well, in order to get an approximate porosity evaluation. This quick scan may allow for immediate core evaluation, and may be used for prompt verification of petrophysics logging measurements. If numerous cores are taken from various locations within an oil field, then a field-wide "sweet spot" can potentially be determined.

Figure 9:
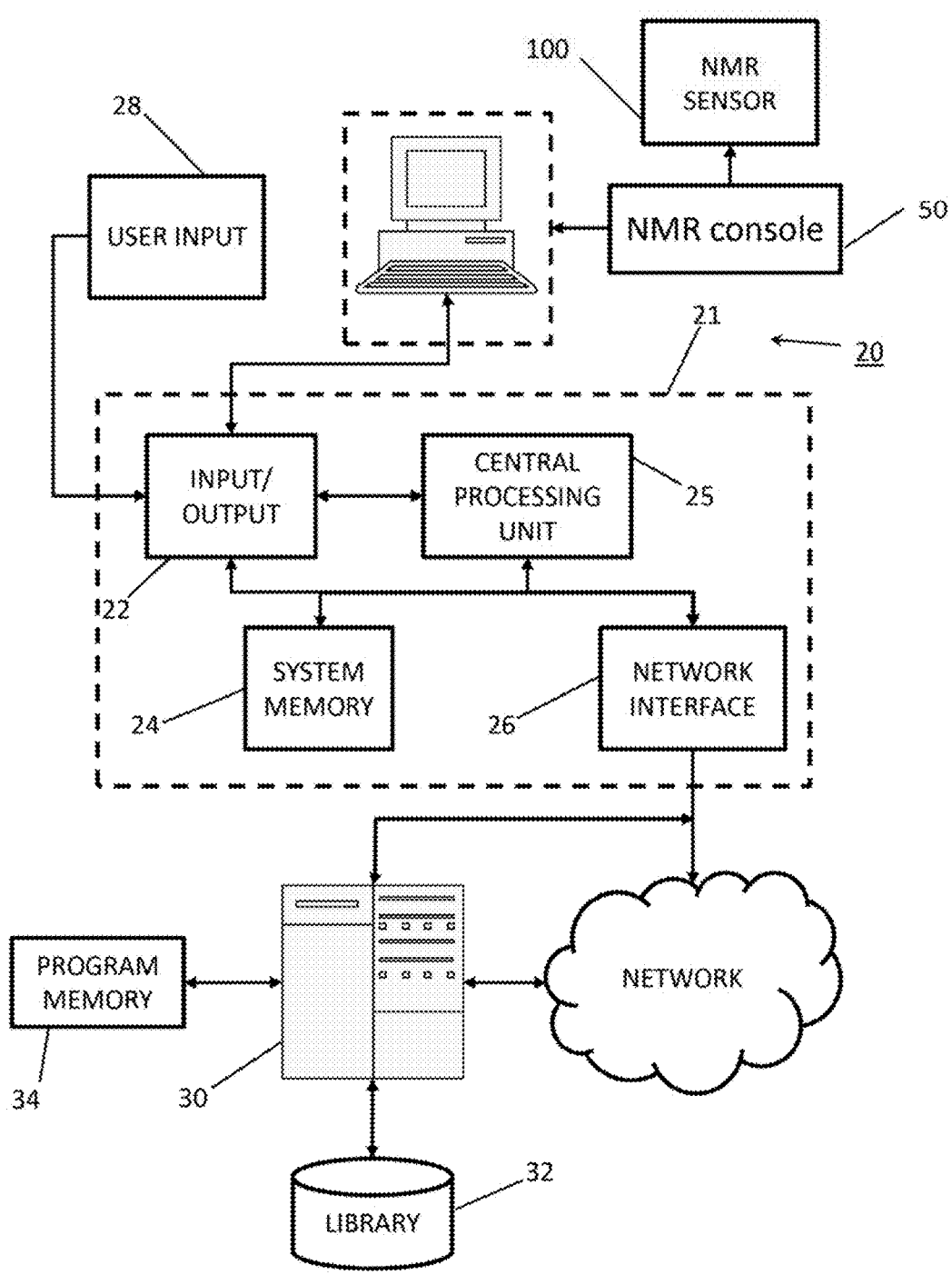
FIG. 9 illustrates a schematic of a system which may be used in conjunction with embodiments of the NMR sensor and associated methods.

FIG. 9 illustrates, according to an example of an embodiment of a system 20, which may perform the operations described in this specification to perform the operations disclosed in this specification. In this example, system 20 is as realized by way of a computer system including NMR sensor 100 connected to a workstation 21 which may be connected to server 30 by way of a network. As mentioned, NMR sensor 100, although depicted as a block, may be any embodiment of the sensor 100 disclosed herein. Of course, the particular architecture and construction of a computer system useful in connection with this invention can vary widely. For example, system 20 may be realized by a single physical computer, such as a conventional workstation or personal computer, or alternatively by a computer system implemented in a distributed manner over multiple physical computers. Accordingly, the generalized architecture illustrated in FIG. 9 is provided merely by way of example.

Figure 10:
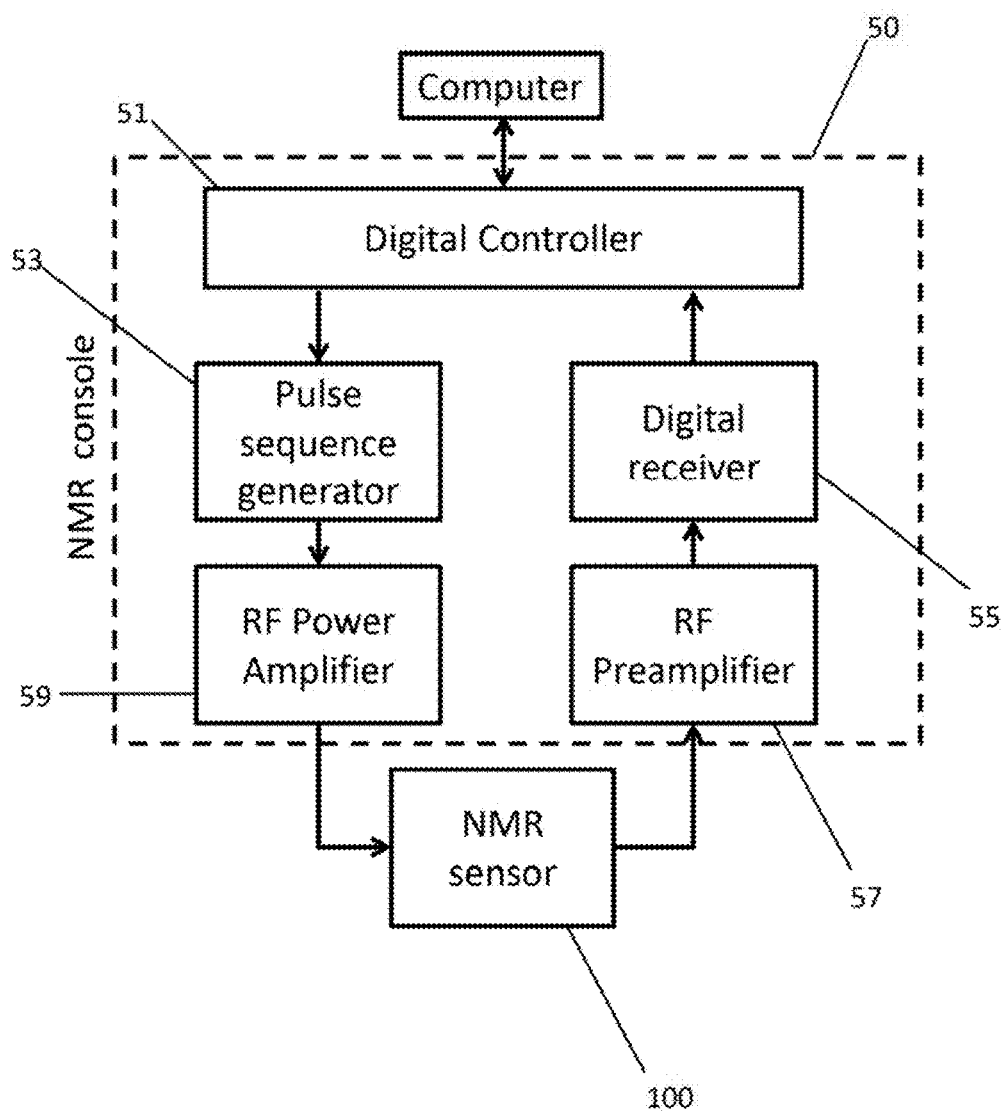
FIG. 10 illustrates a schematic of an NMR console which may be used with embodiments of the NMR sensor.

As shown in FIG. 9 and as mentioned above, system 20 may include workstation 21, NMR sensor 100, and server 30. In an embodiment, NMR sensor 100 may be coupled to an NMR console 50, which also may be coupled to a system 20. FIG. 10 illustrates an NMR console 50 which may be used in conjunction with embodiments of the sensor. NMR console 50 may include without limitation, a digital controller 51, a pulse sequence generator 53, a digital receiver 55, RF power amplifier 59 and an RF preamplifier 57. Other components as are known to those of skill in the art may be included in the NMR console. Although one configuration of an NMR console is shown in FIG. 10, any NMR consoles known to those of skill in the art may be used.

Of course, the particular architecture and construction of a computer system or NMR console 50 useful in connection with this invention can vary widely. Workstation 21 includes central processing unit 25, coupled to system bus. Also coupled to system bus is input/output interface 22, which refers to those interface resources by way of which peripheral functions P (e.g., keyboard, mouse, display, etc.) interface with the other constituents of workstation 21. Central processing unit 25 refers to the data processing capability of workstation 21, and as such may be implemented by one or more CPU cores, co-processing circuitry, and the like. The particular construction and capability of central processing unit 25 is selected according to the application needs of workstation 21, such needs including, at a minimum, the carrying out of the functions described in this specification, and also including such other functions as may be executed by computer system. In the architecture of allocation system 20 according to this example, system memory 24 is coupled to system bus, and provides memory resources of the desired type useful as data memory for storing input data and the results of processing executed by central processing unit 25, as well as program memory for storing the computer instructions to be executed by central processing unit 25 in carrying out those functions. Of course, this memory arrangement is only an example, it being understood that system memory 24 may implement such data memory and program memory in separate physical memory resources, or distributed in whole or in part outside of workstation 21. In addition, as shown in FIG. 9 parameter inputs 28 may be input via input/output function 22, and stored in a memory resource accessible to workstation 21, either locally or via network interface 26.

Network interface 26 of workstation 21 is a conventional interface or adapter by way of which workstation 21 accesses network resources on a network. As shown in FIG. 9 the network resources to which workstation 21 has access via network interface 26 includes server 30, which resides on a local area network, or a wide-area network such as an intranet, a virtual private network, or over the Internet, and which is accessible to workstation 21 by way of one of those network arrangements and by corresponding wired or wireless (or both) communication facilities. In this embodiment of the invention, server 30 is a computer system, of a conventional architecture similar, in a general sense, to that of workstation 21, and as such includes one or more central processing units, system buses, and memory resources, network interface functions, and the like. According to this embodiment of the invention, server 30 is coupled to program memory 34, which is a computer-readable medium that stores executable computer program instructions, according to which the operations described in this specification are carried out by allocation system 30. In this embodiment of the invention, these computer program instructions are executed by server 30, for example in the form of a "web-based" application, upon input data communicated from workstation 21, to create output data and results that are communicated to workstation 21 for display or output by peripherals P in a form useful to the human user of workstation 21. In addition, library 32 is also available to server 30 (and perhaps workstation 21 over the local area or wide area network), and stores such archival or reference information as may be useful in allocation system 20. Library 32 may reside on another local area network, or alternatively be accessible via the Internet or some other wide area network. It is contemplated that library 32 may also be accessible to other associated computers in the overall network.

The particular memory resource or location at which the measurements, library 32, and program memory 34 physically reside can be implemented in various locations accessible to allocation system 20. For example, these data and program instructions may be stored in local memory resources within workstation 21, within server 30, or in network-accessible memory resources to these functions. In addition, each of these data and program memory resources can itself be distributed among multiple locations. It is contemplated that those skilled in the art will be readily able to implement the storage and retrieval of the applicable measurements, models, and other information useful in connection with this embodiment of the invention, in a suitable manner for each particular application.

According to this embodiment, by way of example, system memory 24 and program memory 34 store computer instructions executable by central processing unit 25 and server 30, respectively, to carry out the disclosed operations described in this specification. These computer instructions may be in the form of one or more executable programs, or in the form of source code or higher-level code from which one or more executable programs are derived, assembled, interpreted or compiled. Any one of a number of computer languages or protocols may be used, depending on the manner in which the desired operations are to be carried out. For example, these computer instructions may be written in a conventional high level language, either as a conventional linear computer program or arranged for execution in an object-oriented manner. These instructions may also be embedded within a higher-level application. Such computer-executable instructions may include programs, routines, objects, components, data structures, and computer software technologies that can be used to perform particular tasks and process abstract data types. It will be appreciated that the scope and underlying principles of the disclosed methods are not limited to any particular computer software technology. For example, an executable web-based application can reside at program memory 34, accessible to server 30 and client computer systems such as workstation 21, receive inputs from the client system in the form of a spreadsheet, execute algorithms modules at a web server, and provide output to the client system in some convenient display or printed form. It is contemplated that those skilled in the art having reference to this description will be readily able to realize, without undue experimentation, this embodiment of the invention in a suitable manner for the desired installations. Alternatively, these computer-executable software instructions may be resident elsewhere on the local area network or wide area network, or downloadable from higher-level servers or locations, by way of encoded information on an electromagnetic carrier signal via some network interface or input/output device. The computer-executable software instructions may have originally been stored on a removable or other non-volatile computer-readable storage medium (e.g., a DVD disk, flash memory, or the like), or downloadable as encoded information on an electromagnetic carrier signal, in the form of a software package from which the computer-executable software instructions were installed by allocation system 20 in the conventional manner for software installation.

EXAMPLE

Experimental

Experiments were performed using a Tecmag NMR console (either Apollo or LapNMR) and a Tomco RF amplifier. The consoles were controlled using Tecmag's TNMR software. For the simple CPMG sequence, a wait time of 200 ms was used for samples with relaxed water (water doped with MnCl2), and 1 s was used for samples with standard brine. For the 2D NMR demonstrations, we used an in-house pulse sequence for $T_1$ $T_2$ measurements, and an in-house pulse sequence for $DT_2$ measurements. Pulse lengths of 3.0 μs and 4.5 μs for the 90° and 180° pulses were used, respectively (note that in the presence of a strong magnetic field gradient, the optimal tip angle for the refocusing pulse is in fact less than 180°). The circuit was tuned with a custom built tuning box based on the circuit drawn in FIG. 8, with two variable capacitors for tuning (grounded to the chassis) and matching (kept floating).

Figure 1H:
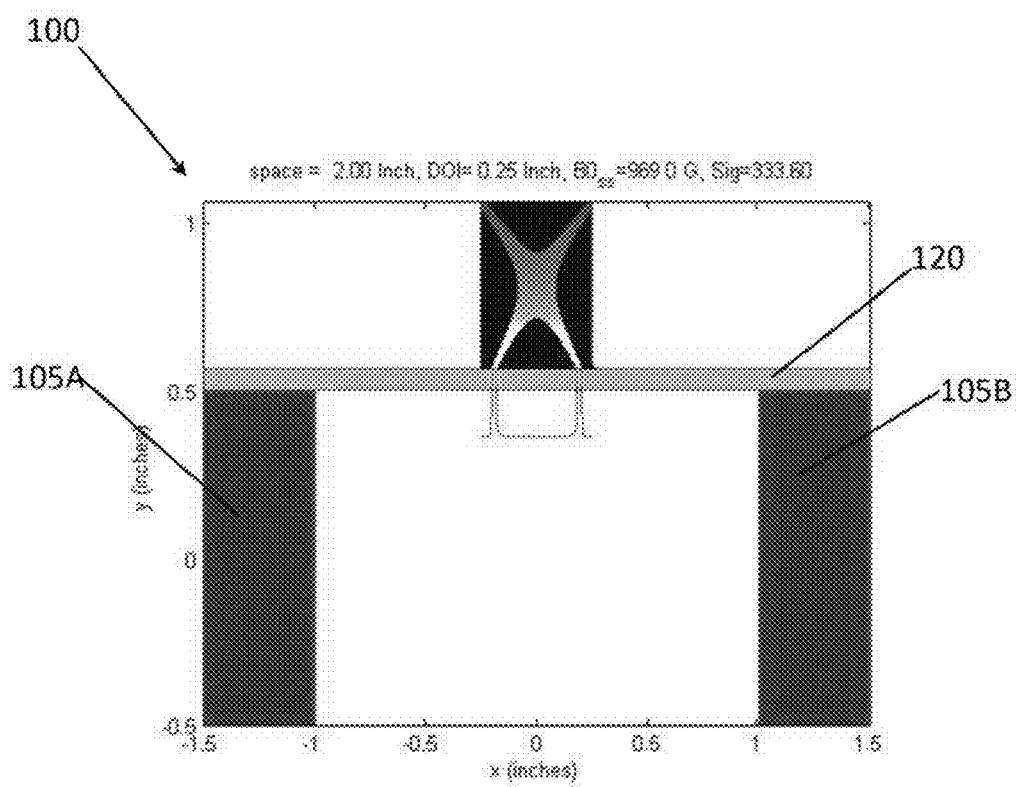
FIG. 1H illustrates an embodiment of the NMR sensor; including a computer simulation of the sweet spot of the sensor.

The prototype design was optimized using a numerical computer model of the field produced by the magnets in a given configuration, with examples shown in FIGS. 1G-1H. In the case of the prototype, the magnets 105A and 105B are separated by 1.2 inches. The prototype model did not include the effects of the steel base, so the calculated field of 0.21 T (2100 G) at the saddle point is slightly lower than the measured field of 0.23 T given by the assembled device. The saddle point had a lateral size of several mm, setting the resolution of the sensor (which may also be referred to as the Scanning Porosity Tool (SPOT) for purpose of this specification), but again this does not consider the effects of the steel base. Modeling with a multiphysics package may be performed for a more accurate calculation of the saddle point size and shape. By considering the field strength, spot size, and relative NMR signal intensity, the sensor may be tailored for a particular application. For example, a larger spot size generally correlates with the spot being further away from the magnets, and thus, the weaker field strength; by tilting the magnets inward, as in FIG. 1G, the sweet spot may be brought closer to the device without significant loss in size.

Results

Figure 3:
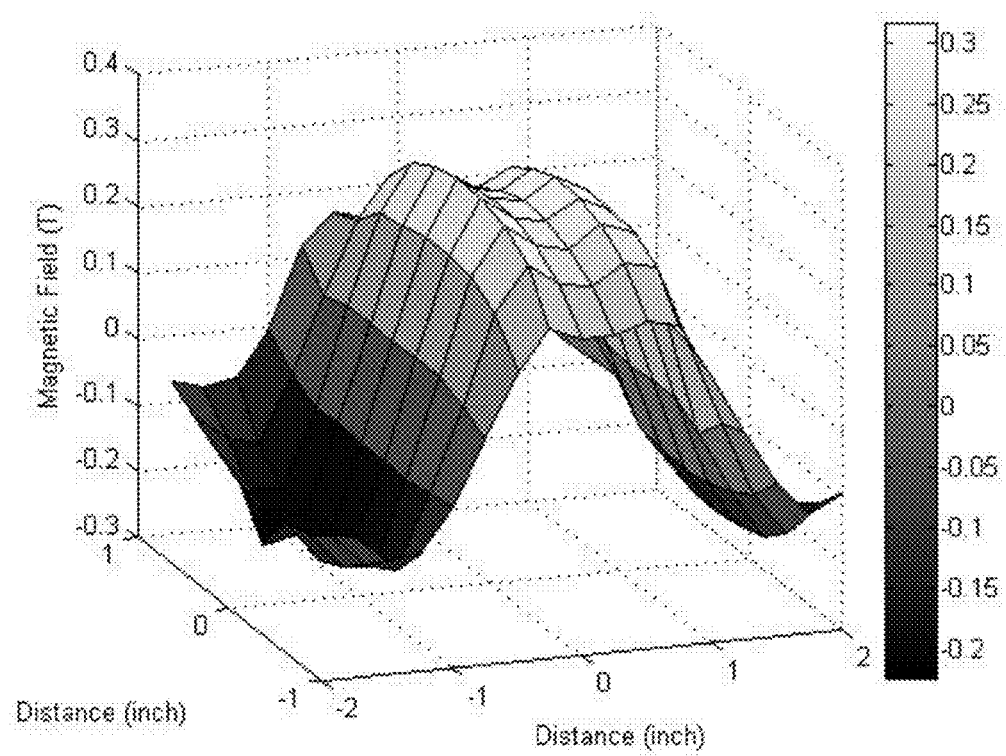
FIG. 3 illustrates the magnetic field component $B_x$ measured at the surface of an embodiment of the sensor, where x is the horizontal axis, showing a saddle point with field of 0.27 T

A prototype of the sensor was assembled with magnet separation of 1.0 inches, the "SPOT-B". The measured magnetic field profile of the device at and near the detection region (right above the surface of the device) is shown in FIG. 3. As expected, the magnetic field exhibits a saddle point in between the magnets that forms the sweet spot; the field has a local minimum at this point, but it is also more homogeneous than in the regions with maximal field. The strength of the field at the saddle point was measured to be 0.27 T, corresponding to a proton resonance frequency of 11.5 MHz.

Figure 4A:
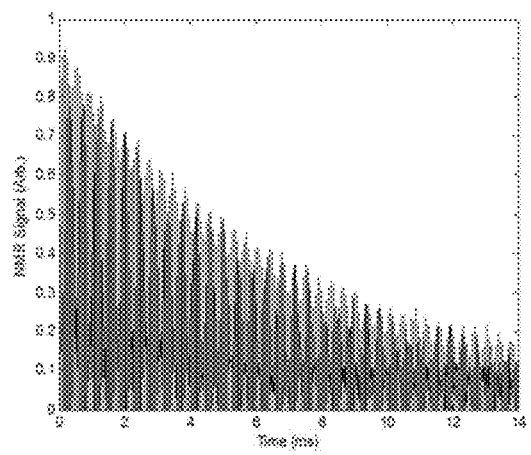
FIG. 4A shows an NMR echo train signal of relaxed water taken with an embodiment of the NMR sensor, with TE=60 µs.
Figure 4B:
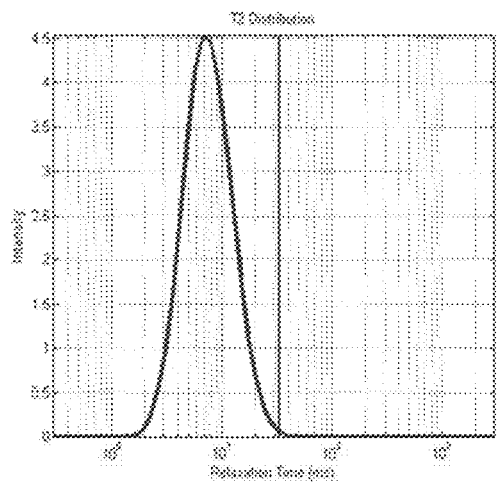
FIG. 4B shows and inversion of the echo train data, showing a spin-spin relaxation time ($T_2$) peak at 7.5 millisecond (ms)
Figure 5A:
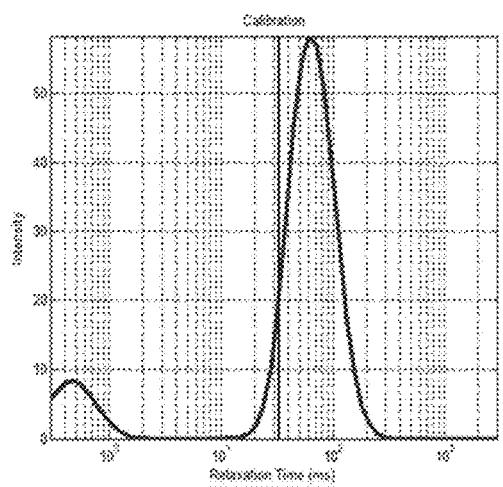
FIG. 5A shows the $T_2$ relaxation spectrum of a bulk relaxed water calibration.
Figure 5B:
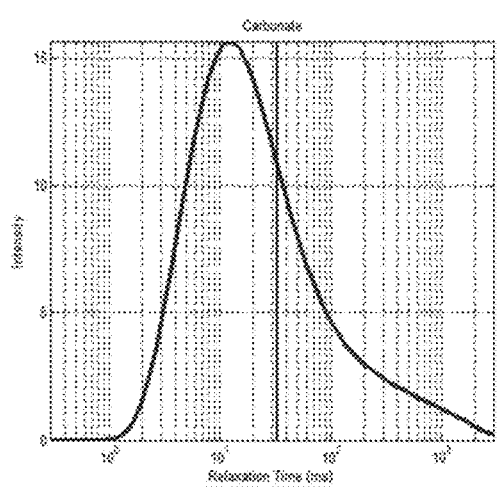
FIG. 5B show the $T_2$ relaxation spectrum of a carbonate core plug which yields a porosity for the plug of 60 porosity units (pu)

Another prototype was assembled with a magnet separation of 1.2 inches (the "SPOT-C"), and was used to successfully demonstrate proton NMR detection. The signal was optimized at approximately 9.7 MHz, higher than expected from the computer simulation and slightly lower than expected from the field measurement (0.23 T, corresponding to 9.8 MHz). The prototype left space between the magnets and the detection region; other embodiments of the sensor may minimize this space to further increase the detection frequency, and thus potentially enhance the NMR signal. Data from a simple Carr-Purcell-Meiboom-Gill (CPMG) echo sequence taken with water ("relaxed" water, which has been doped with $MnCl_2$ salt to have a short spin relaxation time) are shown in FIGS. 4A-4B. Here the spacing between echoes (TE, or "echo spacing") was 60 μs, the wait time between CPMG sequences was 200 ms, and there were 256 scans. For comparison, for any logging tool TE is at least several hundred μs, and for laboratory equipment it tends to also be at least 200 μs (for example, on many 2 MHz NMR core analyzers). Shorter TE enables measurement of shorter relaxation time components, such as very heavy oils and fluids in very small pores (e.g., in shales). Based on inversion of the data, sensitivity is estimated to be approximately 1.5 pu after measuring for 1 minute. FIGS. 5A-5B show a comparison of data taken of a bulk water calibration (defined as 100 pu; a different amount of doping results in a longer relaxation time than in FIGS. 4A-4B) and of a carbonate core plug, yielding a porosity measurement of 60 pu for the plug, in good agreement with a standard laboratory 2 MHz NMR measurement of 57.8 pu. Here the echo spacing was 60 μs, the wait time was 1 s, and there were 64 scans.

Figure 6:
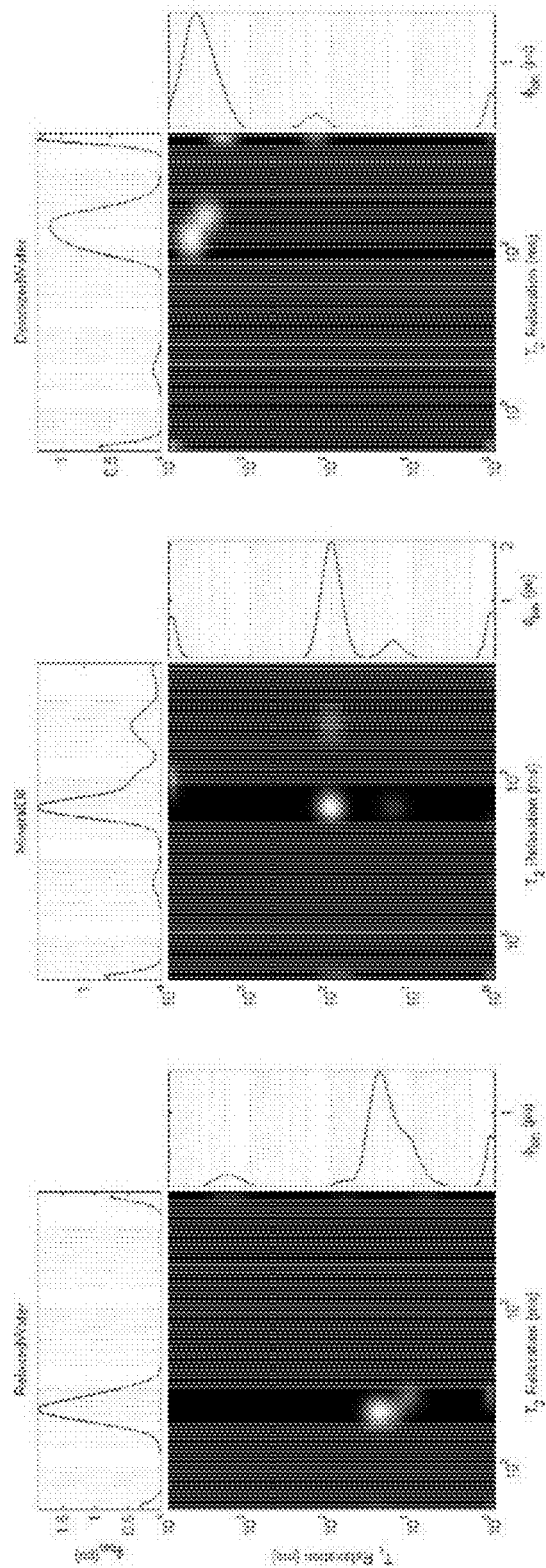
FIG. 6 shows a demonstration of $T_1T_2$ two-dimensional (2D) NMR with an embodiment of the NMR sensor for three bulk fluid samples: relaxed water (the same sample as in FIG. 5A), mineral oil, and deionized water. $T_1$ refers to the spin-lattice relaxation time as is known in the art.
Figure 7:
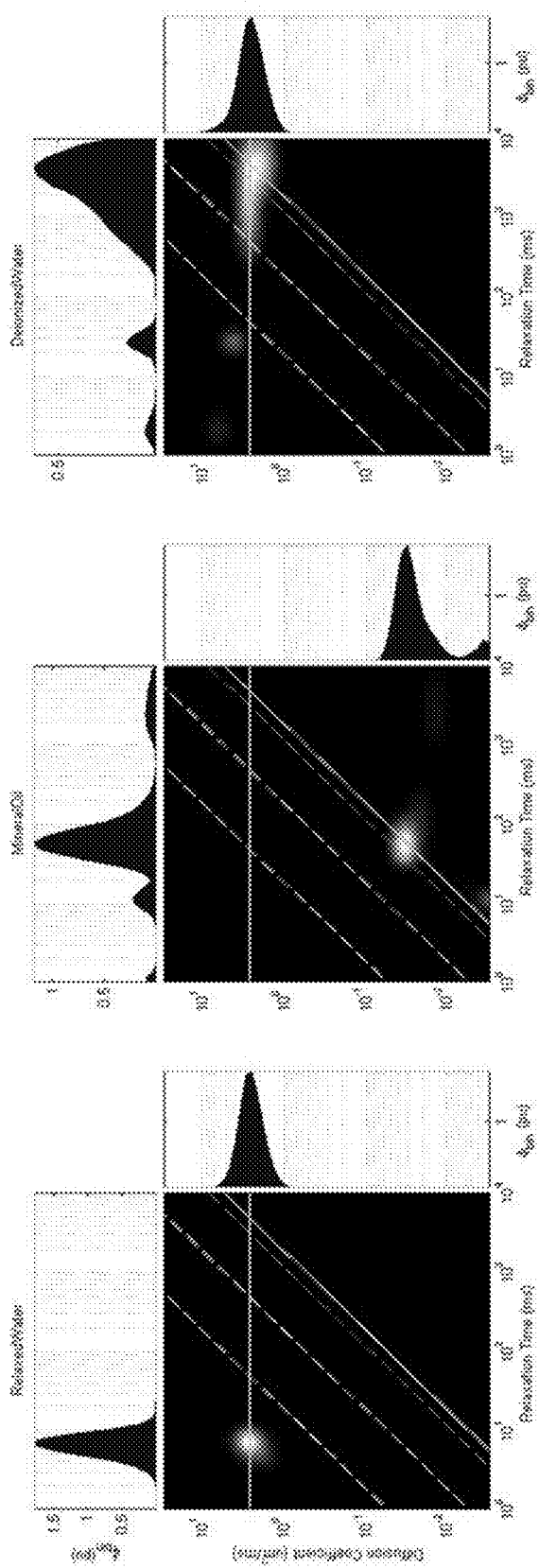
FIG. 7 illustrates a demonstration of diffusion-$T_2$ 2D NMR with an embodiment of the NMR sensor for three bulk fluid samples: relaxed water (the same as in FIG. 5A), mineral oil, and deionized water.

The "SPOT-C" sensor prototype was also applied to two-dimensional NMR. In FIG. 6, we show $T_1T_2$ spectra recorded for three bulk fluid samples: relaxed water (the same sample as used for the data in FIG. 5A) with $T_1$=19.8 ms and $T_2$=10.5 ms, the latter in good agreement with the value $T_2$=7.5 ms as measured by CPMG; mineral oil with $T_1$=84.5 ms and $T_2$=48.7 ms; and deionized water with $T_1$=1885 ms and $T_2$=165.2 ms. FIG. 7 also shows diffusion-$T_2$ spectra measured with the SPOT-C using the same three fluid samples, demonstrating the usefulness of this method for discriminating between water and oil; both water samples lie along the horizontal line, which represents the expected diffusion coefficient of water, while the mineral oil sample lies along the diagonal solid line that represents the typical trend for oil. Note that the diffusion measurements better account for the effect of the strong magnetic field gradient on $T_2$ relaxation time, so the measured value of $T_2$ for the deionized water sample (1.3 s) is significantly greater than in the $T_1T_2$ measurement.

While the embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A single-sided nuclear magnetic resonance (NMR) sensor comprising:
    two or more permanent magnets disposed proximate to each other, wherein the magnets are configured to create a magnetic field;
    a sample holding member coupled to the magnets for holding a sample, wherein the magnetic field is located in a position between the magnets and proximate the surface of the sample holding member such that the magnetic field is outside of the NMR sensor, and wherein the magnetic field comprises a sweet spot outside of the NMR sensor, and wherein the sweet spot is a local extremum in magnetic field strength and serves as a detection volume for the NMR sensor, and wherein the sweet spot has a resolution of about 0.25 inches or less; and
    a radiofrequency antenna comprising a high-permeability magnetic material disposed in between the magnets to guide a plurality of magnetic flux lines from the sweet spot to inside of the NMR sensor, to the sweet spot from the antenna of the NMR sensor, or both.

2. The NMR sensor of claim 1, wherein the magnets are enclosed by a plurality of wall members.

3. The NMR sensor of claim 1, wherein the magnets comprise neodymium magnets.

4. The NMR sensor of claim 1, wherein the magnets comprise a rectangular cross-section.

5. The NMR sensor of claim 1, further comprising more than two magnets.

6. The NMR sensor of claim 1, wherein the magnets have magnetic fields which are opposite one another.

7. The NMR sensor of claim 1, wherein the magnets are disposed at an angle from each other.

8. The NMR sensor of claim 1, wherein the magnets are parallel to each other.

9. The NMR sensor of claim 1, wherein the magnets have a strength ranging from about 1.0 Tesla to about 1.6 Tesla.

10. The NMR sensor of claim 1, wherein proton magnetic resonance frequency resulting from the magnetic field at the sweet spot created by the magnets ranges from about 5 MHz to about 15 MHz.

11. The NMR sensor of claim 1, further comprising a spacer disposed between the magnets.

12. The NMR sensor of claim 11, wherein the spacer is non-magnetic.

13. The NMR sensor of claim 1, further comprising a tuning capacitor.

14. The NMR sensor of claim 1, wherein the antenna comprises a semi-toroidal geometry, a semi-cylindrical geometry, or a rectangular geometry.

15. The NMR sensor of claim 1, wherein the antenna is disposed within the sample holding member.

16. A system for analyzing a sample from a subsurface formation, the system comprising:
    a single-sided nuclear magnetic resonance (NMR) sensor comprising:
        two or more permanent magnets disposed proximate to each other, wherein the magnets are configured to create a magnetic field,
        a sample holding member coupled to the magnets for holding a sample, wherein the magnetic field is located in a position between the magnets and proximate the surface of the sample holding member such that the magnetic field is outside of the NMR sensor, and wherein the magnetic field comprises a sweet spot outside of the NMR sensor, and wherein the sweet spot is a local extremum in magnetic field strength and serves as a detection volume for the NMR sensor, and wherein the sweet spot has a resolution of about 0.25 inches or less, and
        a radiofrequency antenna comprising a high-permeability magnetic material disposed in between the magnets to guide a plurality of magnetic flux lines from the sweet spot to inside of the NMR sensor, to the sweet spot from the antenna of the NMR sensor, or both;
    an interface for receiving one or more user inputs;
    a memory resource;
    input and output functions for presenting and receiving communication signals to and from a human user;
    one or more central processing units for executing program instructions coupled to the NMR sensor and configured to receive one or more signals from the NMR sensor; and program memory, coupled to the central processing unit, for storing a computer program including program instructions that, when executed by the one or more central processing units, cause the system to perform a plurality of operations for analyzing a sample from a subsurface formation.

17. The system of claim 16, further comprising an NMR console coupled to the NMR sensor.

18. The system of claim 16, wherein the magnets are disposed at an angle from each other.

19. The system of claim 16, wherein the magnets are parallel to each other.

20. A method of analyzing a sample from a subsurface formation, the method comprising:
    a) extracting a sample from a subsurface formation;
    b) using a single-sided nuclear magnetic resonance (NMR) sensor to scan the sample by moving the NMR sensor relative to a surface of the sample to determine one or more properties of the sample, the NMR sensor comprising:
        two or more permanent magnets disposed proximate to each other, wherein the magnets are configured to create a magnetic field;
        a sample holding member coupled to the magnets for holding a sample, wherein the magnetic field is located in a position between the magnets and proximal the surface of the sample holding member such that the magnetic field is outside of the NMR sensor, and wherein the magnetic field comprises a sweet spot outside of the NMR sensor, and wherein the sweet spot is a local extremum in magnetic field strength and serves as a detection volume for the NMR sensor, and wherein the sweet spot has a resolution of about 0.25 inches or less; and a radiofrequency antenna comprising a high-permeability magnetic material disposed in between the magnets to guide a plurality of magnetic flux lines from the sweet spot to inside of the NMR sensor, to the sweet spot from the antenna of the NMR sensor, or both; and c) using the determined one or more properties to create a map of the one or more properties of the sample.

21. The method of claim 20, wherein (b) is performed at a well site.

22. The method of claim 20, wherein (b) comprises scanning an entire length of the sample with the NMR sensor.

23. The method of claim 20, wherein (b) comprises placing the sample on to the NMR sensor.

24. The method of claim 20, wherein the one or more properties comprises porosity, $T_1$ or $T_2$ relaxation times, a diffusion coefficient (D), permeability, or combinations thereof.

25. The method of claim 20, wherein the sample is extracted from a shale subsurface formation.

26. The method of claim 20, wherein the sample is extracted from a heavy oil subsurface formation.

27. The method of claim 20, wherein the magnets are disposed at an angle from each other.

28. The system of claim 20, wherein the magnets are parallel to each other.

29. The NMR sensor of claim 1, wherein the NMR sensor is utilized to scan the sample by moving the NMR sensor relative to a surface of the sample to determine one or more properties of the sample, and wherein the determined one or more properties are utilized to create a map of the one or more properties of the sample.

30. The NMR sensor of claim 29, wherein the determined one or more properties are combined with other petrophysical measurements taken at same locations to create an overall petrophysical model of the sample.

31. The NMR sensor of claim 30, wherein the other petrophysical measurements comprise resistivity, permeability, hardness, or any combination thereof.

32. The NMR sensor of claim 1, wherein the NMR sensor is utilized to scan the sample by moving the NMR sensor relative to a surface of the sample to determine porosity values of the sample, and wherein the determined porosity values are utilized to create a map of porosity of the sample.

33. The NMR sensor of claim 32, wherein the porosity values are combined with other petrophysical measurements taken at same locations to create an overall petrophysical model of the sample.

34. The NMR sensor of claim 33, wherein the other petrophysical measurements comprise resistivity, permeability, hardness, or any combination thereof.

35. The system of claim 16, wherein the plurality of operations for analyzing the sample from the subsurface formation comprises scanning the sample by moving the NMR sensor relative to a surface of the sample to determine one or more properties of the sample, and wherein the determined one or more properties are utilized to create a map of the one or more properties of the sample.

36. The system of claim 35, wherein the determined one or more properties are combined with other petrophysical measurements taken at same locations to create an overall petrophysical model of the sample.

37. The system of claim 36, wherein the other petrophysical measurements comprise resistivity, permeability, hardness, or any combination thereof.

38. The system of claim 16, wherein the plurality of operations for analyzing the sample from the subsurface formation comprises scanning the sample by moving the NMR sensor relative to a surface of the sample to determine porosity values of the sample, and wherein the determined porosity values are utilized to create a map of porosity of the sample.

39. The system of claim 38, wherein the porosity values are combined with other petrophysical measurements taken at same locations to create an overall petrophysical model of the sample.

40. The system of claim 39, wherein the other petrophysical measurements comprise resistivity, permeability, hardness, or any combination thereof.

41. The method of claim 20, wherein the determined one or more properties are combined with other petrophysical measurements taken at same locations to create an overall petrophysical model of the core sample.

42. The method of claim 41, wherein the other petrophysical measurements comprise resistivity, permeability, hardness, or any combination thereof.

43. The method of claim 20, wherein the NMR sensor is utilized to scan the sample to determine porosity values of the sample, and wherein the determined porosity values are utilized to create a map of porosity of the sample.

44. The method of claim 43, wherein the porosity values are combined with other petrophysical measurements taken at same locations to create an overall petrophysical model of the sample.

45. The method of claim 44, wherein the other petrophysical measurements comprise resistivity, permeability, hardness, or any combination thereof.

* * * * *